(12) United States Patent
Oh-Lee et al.

(10) Patent No.: US 8,211,459 B2
(45) Date of Patent: Jul. 3, 2012

(54) METHODS OF TREATING DISEASE WITH NITRIC OXIDE (NO)-RELEASING POLYMERS AND SOLUBLE NO-RELEASING NITROSAMINES

(75) Inventors: Justin D. Oh-Lee, Mount Pleasant, MI (US); Dillip K. Mohanty, Mount Pleasant, MI (US)

(73) Assignee: Central Michigan University, Mount Pleasant, MI (US)

( * ) Notice: Subject to any disclaimer, the term of this patent is extended or adjusted under 35 U.S.C. 154(b) by 0 days.

(21) Appl. No.: 13/274,632

(22) Filed: Oct. 17, 2011

(65) Prior Publication Data

US 2012/0034405 A1  Feb. 9, 2012

Related U.S. Application Data

(62) Division of application No. 12/105,857, filed on Apr. 18, 2008, now Pat. No. 8,062,656.

(60) Provisional application No. 60/975,682, filed on Sep. 27, 2007, provisional application No. 60/925,033, filed on Apr. 18, 2007.

(51) Int. Cl.
| | |
|---|---|
| *B32B 1/02* | (2006.01) |
| *B32B 27/34* | (2006.01) |
| *B32B 1/08* | (2006.01) |
| *C08G 73/02* | (2006.01) |
| *A61F 2/08* | (2006.01) |
| *A61F 2/02* | (2006.01) |
| *A61F 2/01* | (2006.01) |
| *A61L 31/06* | (2006.01) |

(52) U.S. Cl. ..... 424/426; 428/35.2; 428/36.9; 428/35.7; 528/422; 525/540

(58) Field of Classification Search .................. None
See application file for complete search history.

(56) References Cited

U.S. PATENT DOCUMENTS

| | | | |
|---|---|---|---|
| 6,379,660 | B1 | 4/2002 | Saavedra et al. |
| 7,776,997 | B2 | 8/2010 | Mohanty et al. |
| 2005/0203272 | A1 | 9/2005 | Mohanty et al. |
| 2006/0155103 | A1 | 7/2006 | Mohanty et al. |
| 2009/0088484 | A1 | 4/2009 | Mohanty |

OTHER PUBLICATIONS

United States Patent Office Action for U.S. Appl. No. 12/105,869 dated Apr. 26, 2011 (19 pages).
Berger et al., "Retrograde degeneration of nigrostriatal neurons induced by intrastriatal 6-hydroxydopamine injection in rates," Brain Research Bulletin (1991) 26:301-307.
Boje, "Nitric oxide neurotoxicity in neurodegenerative diseases," Frontiers in Bioscience (2004) 9:763-776.
Columbia-Presbyterian Medical Center, "Nitric oxide in Parkinson's," Biomedical Frontiers (1997) 4(2):1.
Fingl et al., "The Pharmacological Basis of Therapeutics," Goodman & Gilman's, Chapter 1, p. 1-46 (1975).
Frost et al., "Preparation and characterization of implantable sensors with nitric oxide release coatings," Microchem. J. (2003) 74(3):277-288.
Frost et al., "Polymers incorporating nitric oxide releasing/generating substances for improved biocompatibility of blood-contacting medical devices," Biomaterials (2005) 26(14): 1685-1693.
Gonzalez-Zulueta et al., "Requirement for nitric oxide activation of p21ras/extracellular regulated kinase in neuronal ischemic preconditioning," Proc. Natl. Acad. Sci. (2000) 97: 436-441.
Guix, et al., "The physiology and pathophysiology of nitric oxide in the brain," Progress in Neurobiology (2005) 76: 126-152.
Heales et al., "Neurodegeneration or neuroprotection: the pivotal role of astrocytes," J. Neurochem. Res. (2004) 29 (3): 513-519.
Mohanakumar et al., "Nueroprotection by nitric oxide against hydroxyl radical-induced nigral neurotoxicity," J. Chem. Neuroanat. (1998) 14(3-4): 195-205.
Mohanakumar et al., "Nitric oxide: an antioxidant and neuroprotector," Ann. N.Y. Acad. Sci. (2002) 962: 389-401.
Oh et al., "Protein kinase A inhibitor attenuates levodopa-induced motor response alterations in the hemi-parkinsonian rat," Neuroscience Letters (1997) 228(1): 5-8.
Pan et al., Nitric-oxide-related species inhibit evoked neurotransmission by enhance spontaneous miniature synaptic currents in central neuronal cultures, Proc. Natl. Acad. Sci. USA (1996) 93(26): 15423-15428.
Rauhala et al., "Neuroprotection by S-nitrosoglutathione of brain dopamine neurons from oxidative stress," FASEB J. (1998) 12: 165-173.
Reynolds et al., "Nitric oxide-releasing hydrophobic polymers: preparation, characterization, and potential biomedical applications," Free Radical Biology & Medicine (2004) 37(7): 926-936.
Thomas et al., "L-deprenyl: nitric oxide production and dilation of cerebral blood vessels," NeuroReport (1998) 9(1): 2595-2600.
Tillerson et al. "Exercise induced behavioral recovery and attenuates neurochemical deficits in roden models of Parkinson's disease," Neurosci. (2003) 119: 889-911. Vidwans et al., "Analysis of the neuroprotective effects of various nitric oxide donor compounds in murine mixed cortical cell culture," J. Neurochem. (1999) 72(5): 1843-1852.
Wu et al., "Nitric oxide-releasing/generating polymers for the development of implantable chemical sensors with enhanced biocompatibility," Talanta (2008) 75(3): 642-650.
Zigmond et al., "Pathophysiology of Parkinson's disease," Neuropsychopharmacology: The Fifth Generation of Profess, eds. Davis, K.L. et al., American College of Neuropsychopharmacology (2002) 1781-1794.

*Primary Examiner* — Robert A Wax
*Assistant Examiner* — Danah Al-Awadi
(74) *Attorney, Agent, or Firm* — Michael Best & Friedrich LLP

(57) ABSTRACT

The invention provides NO-releasing polymers and low molecular weight NO-releasing compounds which may be used to for the treatment of medical conditions associated with NO-deficiency. The NO-releasing polymers or the low molecular weight NO-releasing compounds may also be incorporated into medical devices. The invention further provides methods of controlled release of NO for the treatment of diseases and disorders associated with NO-deficiency, wherein the treatment includes systemic or local administration of the NO-releasing polymers or the low molecular weight NO-releasing compounds.

8 Claims, 5 Drawing Sheets

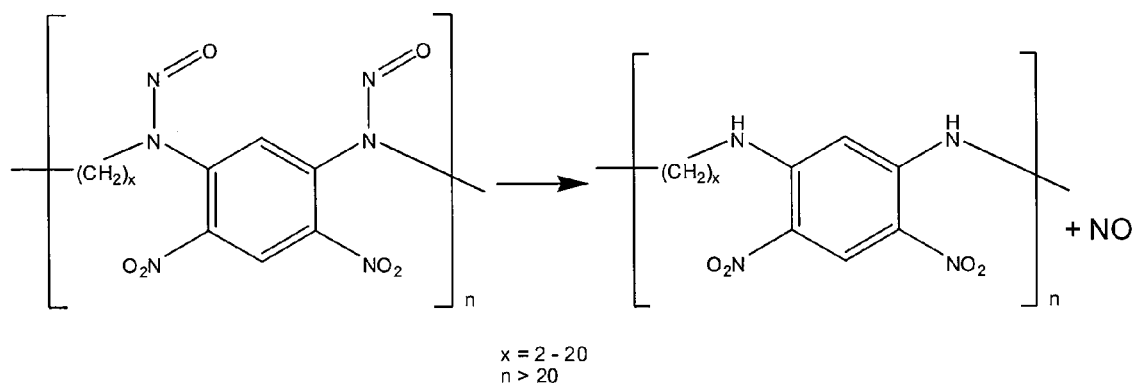
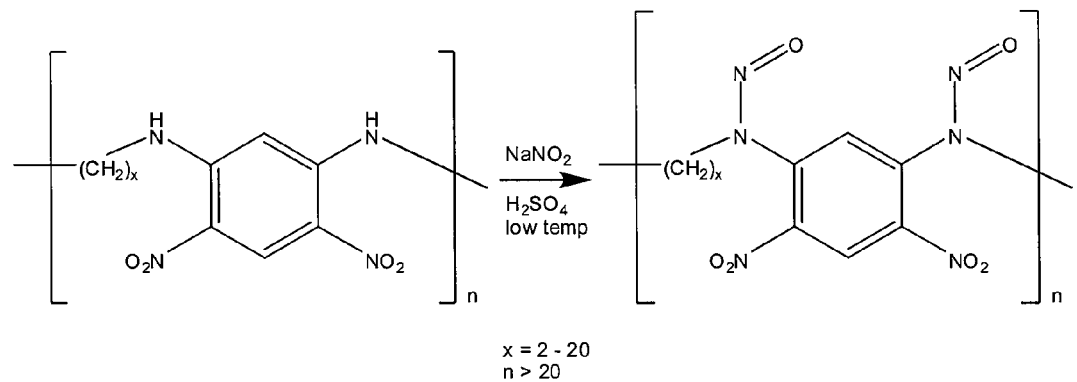
FIG. 1

Number of drug-induced contralateral rotations in hemiparkinsonian rats (control pellet – grey bars; NO-releasing polymer pellet – black filled bars).

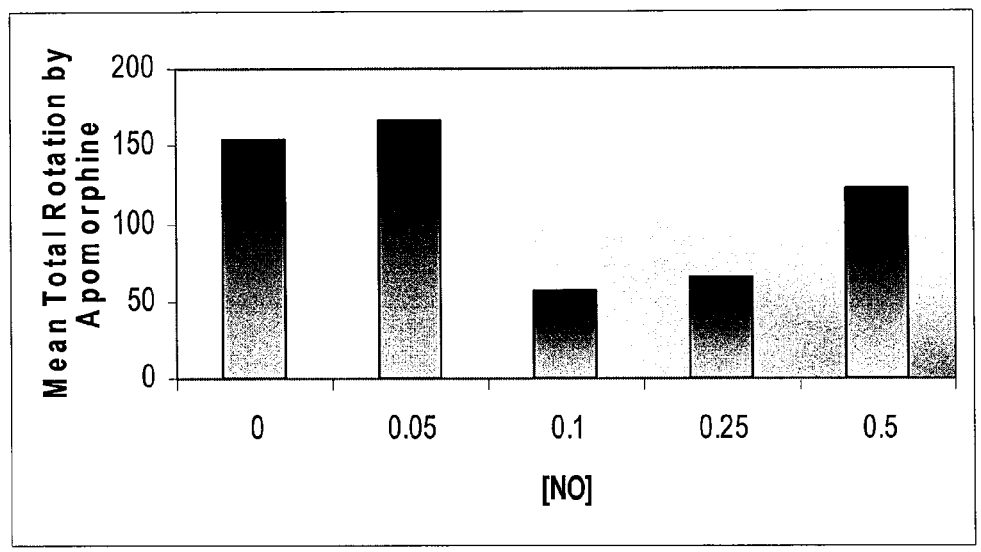

Subcutaneous transplantation of NO-releasing polymeric pellets in dialysis bag significantly attenuated apomorphine-induced contralateral rotations in a dose-dependent manner in hemiparkinsonian rats. The blood plasma concentration of NO was determined by colorimetric analysis of collected blood samples. Concentrations are expressed in millimolar (mM) units.

FIG. 3

Subcutaneous transplantation of NO-releasing polymeric pellets in a dialysis bag increased blood plasma [NO] (mM) and significantly attenuated apomorphine-induced contralateral rotation in hemiparkinsonian rats.

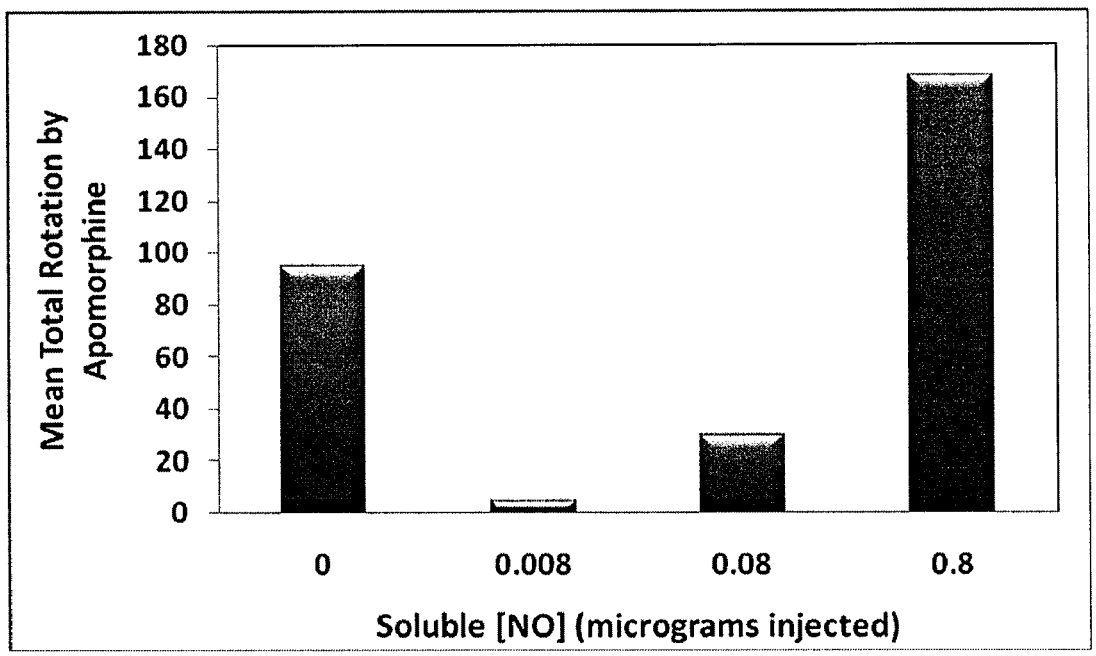

Intracerebral administration with soluble NO-releasing polymeric compound attenuated apomorphine-induced contralateral rotation in a low to medium dose of NO (0.008 to 0.08 μg injected in 2 μL of triethylene glycol dissolved in sterile phosphate buffered saline), but not in a high dose of NO (0.8 μg injected in 2 μL of triethylene glycol dissolved in sterile phosphate buffered saline), in 6-OHDA hemiparkinsonian rats.

FIG. 5

METHODS OF TREATING DISEASE WITH NITRIC OXIDE (NO)-RELEASING POLYMERS AND SOLUBLE NO-RELEASING NITROSAMINES

CROSS-REFERENCE TO RELATED APPLICATIONS

This application is a divisional of U.S. application Ser. No. 12/105,857, filed Apr. 18, 2008, which claims the benefit of priority of U.S. provisional application 60/975,682, filed Sep. 27, 2007 and of U.S. provisional application 60/925,033, filed Apr. 18, 2007. These applications are incorporated herein by reference in their entireties.

BACKGROUND

Parkinson's Disease (PD) is a progressive disorder of the central nervous system affecting over 1.5 million people in the United States. Parkinson's disease is caused by the degeneration of the pigmented neurons in the substantia nigra of the brain, resulting in decreased dopamine availability to the striatum. Clinically, the disease is characterized by an increase in spontaneous movements, gait difficulty, postural instability, rigidity and tremor. Presently, there is no known cause or cure of PD.

The conventional method of treating Parkinson's disease involves the administration of a dopamine agonist, such as levodopa (L-DOPA), administered either alone or in combination with a peripheral dopa decarboxylase inhibitor, such as carbidopa, to a patient suffering from this disorder to restore the nigro-neostriatal hypofunction by increasing the post-synaptic dopamine receptor stimulation. After about 5 years of treatment, however, the majority of PD patients experience a "wearing-off" of drug effect, and often exhibit abnormal motor side effects (e.g., dyskinesias and dystonias) in response to the L-DOPA. It is believed that the development of L-DOPA induced-dyskinesias result from severe nigrostriatal denervation in combination with chronic L-DOPA treatment for a period of time of months to years. These problems limit the long-term benefit that can be achieved with L-DOPA. Once the dyskinesias manifest themselves, the therapeutic options that can be offered to the patient are reduced.

Research in recent years indicates that, depending on neuronal environments, nitric oxide (NO) can initiate and mediate either neuroprotection or neurotoxicity. NO-related agents span the range from prodrugs that elevate NO levels, to scavengers of NO, and inhibitors of endogenous NO synthesis. The term "NO-donor" is used almost universally for NO-related drugs manifesting biological activity that mimics endogenous NO. NO-donors do not fit the traditional receptor-targeted drug design paradigm. NO donors are by definition prodrugs. As prodrugs, NO donors are not readily amenable to in vitro high throughput drug screening. Currently known NO-donors cover a wide range of chemical substances and classes. As such, NO-donors are not expected to manifest identical physiological actions.

BRIEF DESCRIPTION OF THE INVENTION

In accordance with the invention, treatment of diseases and disorders with NO is accomplished by the administration of NO-releasing polymers or low molecular weight NO-donating compounds, which can provide localized, or site specific, NO delivery, i.e., targeted and controlled delivery of NO to the deficient areas in a subject. Polymers and low-molecular weight soluble compounds embodying the principles of the invention may be made of varied lengths and release times for the controlled release of NO. Upon release of NO, inert non-reactive polymeric amines or soluble compounds are formed that are, in fact, the precursors of the NO-releasing polymers or the low molecular weight NO-donating compounds, i.e., the amines can be re-nitrosated to form the NO-releasing polymers or the low molecular weight NO-donating compounds. According to principles embodying the invention, methods of treating a medical condition in which modulating NO level is beneficial are provided.

The invention thus provides methods of treating neurodegenerative, cardiovascular, and gastrointestinal diseases, as well as other medical conditions, including Parkinson's Disease. The invention also provides pharmaceutical compositions for the treatment of these diseases wherein the composition is administered orally, parenterally, or subcutaneously. The invention further provides for a variety of medical devices which incorporate NO-releasing polymers.

BRIEF DESCRIPTION OF THE DRAWINGS

The principles and operation of the invention may be better understood with reference to the accompanying drawings and the following descriptions, in which:

FIG. 1 depicts a NO-donating polymer suitable for use in the invention and the formation of the polymeric amine product;

FIG. 3 is a graph of NO concentration versus Parkinsonian-induced symptoms in Sprague-Dawley rats with using dialysis as the delivery method;

FIG. 5 is a graph representing attenuation of apomorphine-induced contralateral rotation in Sprague-Dawley rats by intracerebral administration of various concentrations of NO-releasing low molecular weight nitrosamines.

DETAILED DESCRIPTION

Figure 2:
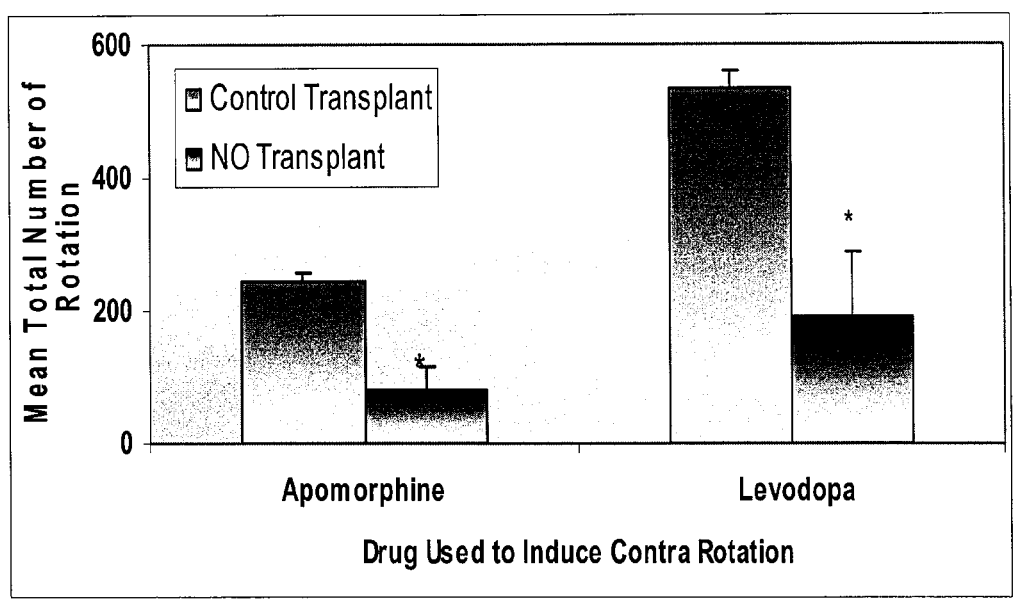
FIG. 2 is a graphic representation of the effect of the NO-donating polymers on Sprague-Dawley rats with Parkinsonian-induced symptoms using direct pellet transplantation.

The invention provides methods of treating diseases utilizing low molecular weight NO-donating compounds or NO-donating polymers (also collectively referred to as NO-donors), which include one or more NO-releasing group(s) covalently linked to a polymeric backbone, and are designed such that NO is released from the polymer or compound under certain conditions. Polymeric amines or soluble amine compounds, formed by NO release, are extremely inert with properties similar to the noble metals. The polymeric amines and soluble compounds are both the precursors of the NO-donors, the amines being nitrosated to form the NO-donating polymers or soluble compounds, and the products of NO-release.

A polymer with —NH— groups is referred to as a secondary amine polymer. A polymer with a —NNO— group is referred to as an N-nitrosamine polymer or simply, NO-releasing polymer. The secondary amine and N-nitrosamine groups are suitably substituted on a substituted aryl group.

The novel NO-donating polymers and the low molecular weight NO-donating compounds of the invention are believed to be of value in the treatment of certain medical conditions, such as ischemic heart disease, heart failure, hypertension and other cardiovascular diseases, blood clotting, blood pressure, and the destruction of cancerous tumor cells, as well as a variety of neurodegenerative diseases, including Parkinson's Disease, Alzheimer's Disease, Huntington Disease, multiple sclerosis, and other related disorders. The invention also contemplates pharmaceutical compositions including the NO-donors, as well as medical devices designed for various modes of delivering the NO-donating polymers or the low molecular weight NO-donating compounds. Medical devices may be suitably constructed of the secondary amine polymers and nitrosated prior to therapeutic use.

The novel NO-donating polymers may suitably include additional functional monomer units known to those of skill in the art. The additional functional monomer units may comprise a cyclic group, a polycyclic group, a branched aliphatic group, or a combination thereof. By adding additional functional monomer units, it is possible to suitably modify the chemo-physical properties of the NO-donating polymers.

It is also envisioned that by conjugating another bioactive or therapeutic compound to the NO-donating polymer in accordance with the invention, or by co-administering another bioactive or therapeutic agent, combined, and even, therapeutic effects could be achieved, resulting from the dual therapeutic effect of the bioactive agent and the NO-releasing group.

Before explaining at least one embodiment of the invention in detail, it is to be understood that the invention is not limited in its application to the details set forth in the following description or exemplified by the Examples. Such description and Examples are not intended to limit the scope of the invention as set forth in the appended claims. The invention is capable of other embodiments or of being practiced or carried out in various ways. For example, while the following detailed description describes the invention through reference to embodiments, e.g., utilizing certain NO-releasing polymers and inert secondary amine polymers, it should be understood that other NO-releasing polymers are also suitable for use with the teachings of the invention. Although methods and materials similar or equivalent to those described herein can be used in the practice or testing of the invention, suitable methods and materials are described below. Also, it is to be understood that the phraseology and terminology employed herein is for the purpose of description and should not be regarded as limiting.

Further, the use of "comprising," "including," "having," and variations thereof herein is meant to encompass the items listed thereafter and equivalents thereof as well as additional items, e.g., that other steps and ingredients that do not affect the final result can be added. This term encompasses the terms "consisting of" and "consisting essentially of". The use of "consisting essentially of" means that the composition or method may include additional ingredients and/or steps, but only if the additional ingredients and/or steps do not materially alter the basic and novel characteristics of the claimed composition or method.

Further, no admission is made that any reference, including any patent or patent document, cited in this specification constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinency of any of the documents cited herein.

Throughout this disclosure, various aspects of this invention may be presented in a range format. It should be understood that the description in range format is merely for convenience and brevity, and should not be construed as an inflexible limitation on the scope of the invention. Accordingly, as will be understood by one skilled in the art, for any and all purposes, particularly in terms of providing a written description, all ranges disclosed herein also encompass any and all possible subranges and combinations of subranges thereof, as well as all integral and fractional numerical values within that range. As only one example, a range of 20% to 40% can be broken down into ranges of 20% to 32.5% and 32.5% to 40%, 20% to 27.5% and 27.5% to 40%, etc. For further example, if a polymer is stated as having 7 to 300 linked monomers, it is intended that values such as 7 to 25, 8 to 30, 9 to 90, or 50 to 300, as well as individual numbers within that range, for example, 25, 50, and 300, are expressly enumerated in this specification. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. Further, as will also be understood by one skilled in the art, all language such as "up to," "at least," "greater than," "less than," "more than," and the like include the number recited and refer to ranges which can be subsequently broken down into subranges as discussed above. In the same manner, all ratios disclosed herein also include all subratios falling within the broader ratio. These are only examples of what is specifically intended. Further, the phrases "ranging/ranges between" a first indicate number and a second indicate number and "ranging/ranges from" a first indicate number "to" a second indicate number are used herein interchangeably.

Unless otherwise defined, all technical and scientific terms used herein have the same meaning as commonly understood by one of ordinary skill in the art to which this invention belongs. However, as used herein, the following definitions may be useful in aiding the skilled practitioner in understanding the invention:

As used herein, the phrase "chemical moiety" refers to a functional group which is a part or component of an organic molecule, and possesses certain chemical properties.

The term "alkyl" refers to a saturated aliphatic hydrocarbon including straight chain and branched chain groups. Preferably, the alkyl group has 1 to 20 carbon atoms. It is again noted that whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The alkyl group can be an end group, wherein it is attached to a single adjacent atom, or a linking group, which connects two or more moieties via at least two carbons in its chain.

The term "aryl" refers to an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, in which each substituent group can independently be, for example, nitro, halo, alkenyl, alkynyl, aryl, heteroaryl, heteroalicyclic, amine, sulfonate, sulfoxide, phosphonate, hydroxy, alkoxy, aryloxy, thiohydroxy, thioalkoxy, thioaryloxy, cyano, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, wherein it is attached to a single adjacent atom, or a linking group, connecting two or more moieties at two or more positions thereof.

The terms "halide" and "halo" refer to fluorine, chlorine, bromine or iodine.

As used herein, the phrase "NO-releasing group" refers to a chemical moiety, which is capable of generating NO either spontaneously or by means of chemical or enzymatic reactions. In accordance with the invention, a suitable NO-releasing group includes, without limitation, an N-nitrosamine group, —NNO—.

As used herein in connection with numerical values, the terms "about" and "approximately" are meant to encompass variations of about ±20%, including ±10% or less of the indicated value.

The term "treating" includes inhibiting, slowing, or reversing the progression of a medical condition, ameliorating or reducing symptoms of a condition, or preventing the appearance of symptoms of a condition.

The term "active ingredient" refers to a pharmaceutical agent that subsequent to its application has, at the very least, one desired pharmaceutical or therapeutic effect.

The term "therapeutically effective amount" or "pharmaceutically effective amount" or simply "effective amount" denotes that dose of an active ingredient or a composition comprising the active ingredient that will provide the therapeutic effect for which the active ingredient is indicated, i.e., relieving to some extent one or more symptoms of the disease being treated, or modulating, e.g., elevating an NO level.

The term "pharmaceutically acceptable carrier" refers to a carrier or a diluent that does not cause significant irritation to an organism and does not abrogate the biological activity and properties of the active ingredient. Examples, without limitations, of carriers are: propylene glycol, saline, emulsions, and mixtures of organic solvents with water, as well as solid (e.g., powdered) and gaseous carriers.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

The term "subject," as used herein, is intended to describe an animal, more typically a mammal, and most typically a human presenting a physiological disorder or disease for which treatment with NO would be beneficial. In some cases, "subject" refers to an animal that receives a treatment for the purposes of comparison, e.g., a control animal, even though the animal does not present a physiological disorder or disease for which treatment with NO would be beneficial.

As used herein, a "pharmaceutical composition" refers to a preparation of one or more of the NO-donating polymers or NO-donating low molecular weight compounds described herein, with other chemical components such as pharmaceutically acceptable and suitable carriers and excipients. The purpose of a pharmaceutical composition is to facilitate administration of the polymer to an organism.

As is conventional, the singular form "a," "an," and "the" include plural references unless the context clearly dictates otherwise. For example, the term "a compound" or "at least one compound" may include a plurality of compounds, including mixtures thereof.

Organic nitrate and nitrite esters represent a time-honored class of NO-donating agents used in cardiovascular therapeutics since the nineteenth century. These agents have direct vasoactive effects, and have therefore, been used to treat ischemic heart disease, heart failure, and hypertension for many years. However, treatment methods utilizing these compounds are severely limited by their therapeutic half-life, systemic absorption that is oftentimes accompanied by adverse hemodynamic effects, and drug tolerance.

The design and preparation of novel NO-donating polymers which upon releasing a bioactive NO, an inert polymer is formed, have been developed. It is contemplated that such NO donors, when entering a biological system, are subjected to enzymatic reactions that result in the release of a bioactive NO and the formation of an inert polymer which is characterized by hydrophobicity and inertness.

NO-donating polymers especially useful in the methods in accordance with the invention include mono- and di-N-nitrosamine monomers represented by general formulas (I)-(III). Formula (I) represents a suitable mono-N-nitrosamine polymer:

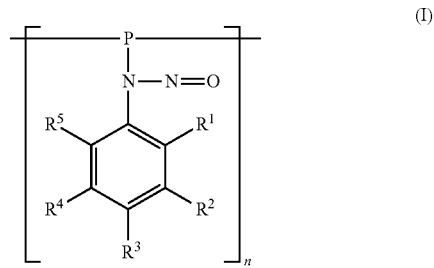

wherein P is a polymeric species with a chemical moiety capable of forming a covalent bond with N, and n is an integer greater than about 20, and $R^1$, $R^2$, $R^3$, $R^4$, and $R^5$ are H, F, or $NO_2$ provided that when $R^1$=F, then $R^2$, $R^3$, $R^4$, and $R^5$=F; and provided that when $R^1$=$NO_2$, then $R^2$, $R^3$, $R^4$, and $R^5$=H; provided that when $R^5$=$NO_2$, then $R^1$, $R^2$, $R^3$, and $R^4$=H; when $R^2$=$NO_2$, then $R^4$=$NO_2$ and $R^1$, $R^3$, and $R^5$=H; and when $R^3$=$NO_2$, then $R^1$, $R^2$, $R^4$, and $R^5$=H.

Formula (II) represents a suitable di-N-nitrosamine polymer:

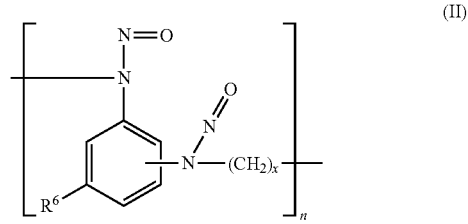

wherein x=2 to 12 and n is an integer greater than about 20, and $R^6$ is $NO_2$, CN, $CF_3$, or phenyl sulfone.

Formula (III) represents another suitable di-N-nitrosamine polymer:

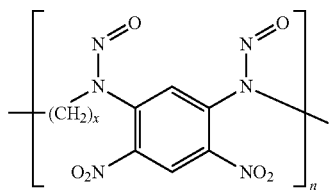

wherein x is 2 to 20 and n is an integer greater than about 20.

The NO-releasing polymers or the low molecular weight NO-donating compounds, in accordance with the invention, include at least one NO-releasing group, as detailed herein. Upon release of NO, e.g., from a polymer of formulas (I)-(III), or a low molecular weight compound of formula (VII) inert, non-reactive, secondary polymeric amines or soluble compounds are formed. The polymeric amine polymers formed from the release of NO from the polymers depicted in formulas (I)-(III) are shown in formulas (IV)-(VI). Formula (IV) is:

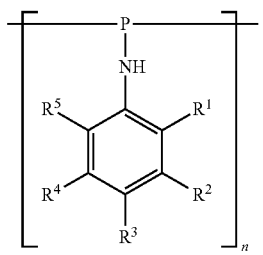

wherein P, n, $R^1$, $R^2$, $R^3$, $R^4$, and $R^5$ have the same meaning as described above for formula (I).

Formula (V) is:

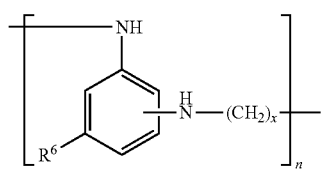

wherein x, n and $R^6$ have the same value as described in formula (II).

Formula (VI) is:

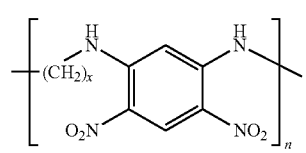

wherein x=2 to 12 and n is an integer greater than about 20.

The methods of synthesizing formulas (I)-(V) are described in co-pending U.S. patent application, "Nitric Oxide (NO)—Releasing Polymers and uses thereof, D. K. Mohanty, inventor, while the method of" synthesizing formula (VI) is described in co-pending application, U.S. Ser. No. 11/346,952, "Solvent Resistant Polymers," Dillip K. Mohanty and Ajit Sharma, inventors. Both of these applications are incorporated by reference in their entireties herein.

The polymeric amines in formula (IV)-(VI) are also the precursors or starting materials for the corresponding NO-releasing polymers (I)-(III), the amines being readily nitrosated to the N-nitrosamine polymers. The interconversion between NO-releasing polymers and secondary polymeric amines is illustrated for formulas (III) and (VI) in FIG. 1.

The polymeric secondary amines are inert and exhibit a solubility profile typical of noble metals, which, in their metallic state, are known to be non-toxic. It is contemplated that such stability and lack of solubility may allow for the use of an implantable therapeutic agent, which undergoes a reaction to produce a non-toxic end product, which cannot undergo further metabolism. In addition, an implant (after NO dissipation) may also be removed from the body.

The NO-donating polymers of the invention are tunable in that the rate of NO release can be varied based upon the structure of the polymer. The NO-release rate may be varied by incorporating NO-donating monomers with lower NO binding constants, by varying the structure of the intervening alkyl chain between monomer units, and/or by altering the distance between the substituted aryl and the secondary amine which donates the NO.

As is demonstrated in the Examples below, the polymers described above were found to be active NO-donating agents and were found to cover a range of release times, which is indicative of the tunability of the polymers to controlled NO release. By tuning the polymers, it is possible to vary the release time from several hours to many days. Typically, the polymers are tuned to release the NO for more than one hour, but for less than about 30 days. In a series of in vivo tests, the NO-donors according to the invention were found effective in treating, i.e., reducing, the symptoms of Parkinson's Disease induced in a model system. These results indicate that the NO-donating polymers of the invention may be beneficially used in the treatment of neurodegenerative and medical conditions associated with NO deficiency.

As noted above, the invention further contemplates the use of low-molecular-weight, soluble, NO releasing compounds such as formula (VII):

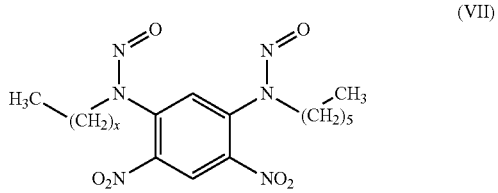

The methods of synthesizing formula (VII) is described in co-pending U.S. patent application, "Nitric Oxide (NO)—Releasing Polymers and uses thereof, D. K. Mohanty, inventor. Like the NO-releasing polymers described herein, these low molecular weight compound are capable of" interconversion between NO-releasing compounds and secondary amines Thus, according to the invention, there is provided a method of treating a medical condition in which modulating an NO level is beneficial. The method, according to this aspect of the invention, is affected by administering to a subject in need thereof a therapeutically effective amount of one or more of the NO-donors described herein.

An exemplary therapeutically effective amount of an NO-donating polymer of the invention ranges between about 35 mg/kg body weight and about 70 mg/kg body weight. A typical unit dosage of the NO-donating polymers of the invention may therefore be equal to or lower than 0.1 mM NO in plasma per 300 g body weight.

Inadequate somatic NO levels are associated with various biological dysfunctions. Administering an NO-donor in accordance with the invention to subjects that suffer from such inadequate somatic NO levels, therefore, may ameliorate the biological dysfunction itself or its symptoms. Thus, neurological or other medical conditions, which are beneficially treatable by the method according to this aspect of the invention, are those in which modulating, e.g., elevating, the NO-level in a subject is beneficial.

In addition to the neurological conditions in which modulating NO level is beneficial, other non-limiting examples of medical conditions in which modulating, and suitably elevating, the NO level is beneficial include cardiovascular diseases or disorders, gastrointestinal diseases or disorders, inflammatory diseases or disorders, respiratory diseases or disorders, central nervous system diseases or disorders, neurodegenerative diseases or disorders, psychiatric diseases or disorders, blood pressure-associated diseases or disorders, coronary artery diseases or disorders, atherosclerosis, cholesterol level-associated diseases or disorders, arterial thrombotic diseases or disorders, a heart failure, a stroke, a septic shock, NSAID-induced gastric diseases or disorders, inflammatory bowel diseases or disorders, ischemic renal diseases or disorders, peptic ulcer, diabetes, pulmonary hypertension, sickle cell anemia, an asthma, chronic obstructive pulmonary disease, dementia, epilepsy, neuroinflammatory diseases or disorders, trauma, multiple sclerosis, erectile dysfunction, other male and female sexual dysfunctions and age-related diseases or disorders.

Pharmaceutical compositions for use in accordance with the invention may be formulated in conventional manner using one or more pharmaceutically acceptable carriers comprising excipients and auxiliaries, which facilitate processing of the NO-donors in accordance with the invention into preparations which can be used pharmaceutically. Such pharmaceutical formulations of the invention may be manufactured by processes well known in the art, e.g., by means of conventional mixing, dissolving, granulating, dragee-making, tablet or pellet-making, emulsifying, encapsulating, entrapping or lyophilizing processes. Proper formulation is dependent upon the route of administration chosen. Techniques for formulation and administration of drugs may be found in "Remington's Pharmaceutical Sciences" Mack Publishing Co., Easton, Pa., latest edition, which is incorporated herein by reference.

The NO-donors according to the invention may be administered orally, rectally, intravenously, intraventricularly, topically, intranasally, intraperitoneally, intestinally, parenterally, intraocularly, intradermally, transdermally, subcutaneously, intramuscularly, transmucosally, by inhalation and/or by intrathecal catheter. In one aspect, the NO-donors, according to the invention, are administered orally or intravenously, and optionally topically, transdermally or by inhalation, depending on the condition and the subject being treated.

For injection, the NO-donating low molecular weight compounds of the invention may be formulated in aqueous solutions, e.g., in physiologically compatible buffers such as Hank's solution, Ringer's solution, or physiological saline buffer with or without organic solvents such as propylene glycol, polyethylene glycol.

The NO-donors described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the NO-donating polymers or the low molecular weight NO-donating compounds prepared in water-soluble form. Additionally, suspensions of the NO-donating polymers or the low molecular weight NO-donating compounds may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the NO-donors to allow for the preparation of highly concentrated solutions.

For transmucosal administration, penetrants are used in the formulation. Such penetrants are generally known in the art.

For oral administration, the NO-donating polymers or the low molecular weight NO-donating compounds of the invention can be formulated readily by combining the NO-donating polymers or the low molecular weight NO-donating compounds with pharmaceutically acceptable carriers well known in the art. Such carriers enable the NO-donors of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores may also be provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active NO-donor doses.

For buccal administration, the compositions may take the form of tablets or lozenges formulated in conventional manner.

Alternatively, the NO-donating polymers or the low molecular weight NO-donating compounds may be in powder form for constitution with a suitable vehicle, e.g., sterile, pyrogen-free water, before use.

The NO-donating polymers or the low molecular weight NO-donating compounds of the invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the invention include compositions wherein the active ingredients are contained in an amount effective to achieve the intended purpose. More specifically, a therapeutically effective amount means an amount of NO-donors effective to prevent, alleviate or ameliorate symptoms of disease in the subject being treated.

For any NO-donating polymers or the low molecular weight NO-donating compounds used in the methods of the invention, the therapeutically effective amount or dose can be estimated initially from activity assays in animals. For example, a dose can be formulated in animal models to achieve a circulating concentration range that includes the $IC_{50}$ as determined by activity assays. Such information can be used to more accurately determine useful doses in humans.

Toxicity and therapeutic efficacy of the NO-donating polymers or the low molecular weight NO-donating compounds described herein can be determined by standard pharmaceutical procedures in experimental animals, e.g., by determining the $EC_{50}$, the $IC_{50}$ and the $LD_{50}$ (lethal dose causing death in 50% of the tested animals) for a subject NO-donor. The data obtained from these activity assays and animal studies can be used in formulating a range of dosage for use in human.

The dosage, however, may vary depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1, p. 1.)

Dosage amount and interval may be adjusted individually to provide plasma levels of the active moiety which are sufficient to maintain the desired effects, termed the minimal effective concentration (MEC). The MEC will vary for each preparation, but can be estimated from in vitro data; e.g., the concentration necessary to achieve 50-90% vasorelaxation of contracted arteries. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, suitably between 30-90% and more suitably 50-90%.

Depending on the severity and responsiveness of the condition to be treated, dosing can also be a single administration of a slow release composition described hereinabove, with course of treatment lasting from several days to several weeks or until therapy is effected or diminution of the disease state is achieved. As described herein, an inherent property of the NO-donating polymers in accordance with the invention is the controlled release of NO over time. Thus, a treatment based upon NO-releasing polymers may be administered daily, weekly, or monthly, depending upon the nature of the administration and the properties of the polymer.

The amount of a composition to be administered will, of course, be dependent on the subject being treated, the severity of the affliction, the manner of administration, as well as the judgment of the prescribing physician.

It is anticipated that the NO-donating polymers of the invention or the secondary polymeric amine precursors can be further beneficially utilized as active substances in various medical devices. According to an additional aspect of the invention, there is provided a medical device which includes one or more of the NO-donating polymers, or the polymeric amine precursors of the invention, described herein, and a delivery system configured for delivering the NO-donating polymer(s) to a bodily site of a subject. The medical devices according to the invention are therefore used for delivering to or applying on a desired bodily site the NO-donating polymers of the invention. The NO-donating polymers can be incorporated in the medical devices either per se or as a part of a pharmaceutical composition, as described hereinabove. It is contemplated that the polymeric amine precursors may be used for the construction of a medical device and suitably converted to NO-donating polymers prior to being used for therapeutic delivery of NO. As used herein, the phrase "bodily site" includes any organ, tissue, including brain, membrane, cavity, blood vessel, tract, biological surface or muscle, which delivering thereto or applying thereon the compounds of the invention is beneficial.

The medical devices according to this aspect of the invention can be any medical device known in the art, including those defined and classified, for example, by the FDA, depending on the condition and bodily site being treated and the therapeutic benefit to modulating NO levels.

Reference is now made to the following examples, which together with the above descriptions, illustrate the invention in a non limiting fashion.

EXAMPLES

Example 1

General Procedure

Delivery of the NO-releasing polymers was accomplished by transplantation into the brain of pellets of the polymer or via a dialysis bag containing such pellets. Pellets of NO-releasing polymer of general formula I (x=10) and secondary diamine of general formula II (x=10) (as control) were prepared by mixing 75 parts by weight of NaCl and 25% by weight of polymer. Mixtures were made into pellets using a press.

The dialysis bag was prepared using cellulose acetate membrane (MW cutoff=100; diameter=10 mm; length=15 mm). Each bag contained various amounts (0.01-1.0 g) of pellet.

Standard rats, such as Sprague Dawley rats, were utilized and were injected with 6-hydroxydopamine (6-OHDA) to produce Parkinsonian symptoms. The NO polymer pellet or dialysis bag was transplanted subcutaneously. Every week for three weeks post-surgery, animals were administered neurological tests (open field monitor, paw placement and drag) to assess their motor symptoms. The open field monitor was a 38.7 cm×38.7 cm chamber that a rat was placed in for a specific period of time, in this case, sixty minutes. During this time, a computer recorded the amount of activity displayed by the rat. The drag test screened for intact reflex ability by dragging a rat across a small carpeted area, and counting the number of foot hops. (A foot hop implies that the limb was functional.) This test is useful for Parkinsonian animals because affected limbs will not react to the dragging. The paw placement test screened for reflex abilities on both the lesion and unaffected sides of the rat by monitoring the animal's response to vibrissae stimulation.

At the end of three week post-surgery, animals were challenged with a dopamine agonist, apomorphine or levodopa, to assess contralateral rotational behavior, an index of Parkinsonian severity. Animals were placed into round buckets in a dimly lit room and the rotation behavior was recorded for two hours using a camera. The number of rotations were counted by analyzing the video tapes. It is believed that the NO signaling pathway, both centrally and peripherally, is intricately related to the pathogenesis of Parkinson's Disease, resulting from nigrostriatal dopaminergic denervation.

Example 2

Study of Polymers in an In Vivo Parkinson's Disease Model System

This study was conducted in accordance with the NIH Guide for the Care and Use of Laboratory Animals. Male Sprague-Dawley rats were housed with free access to food and water, and kept on a 12:12 hours light and dark cycle. The rats were divided into two experimental groups and a control group. Each experimental group consisted of five animals who were housed in pairs. Each animal was weighed routinely. A control group consisted of two animals housed together. These animals were also weighed routinely during the experiment.

All animals were lesioned with 6-OHDA in amounts of 8.0 µg in 4 µL of saline with 0.02% ascorbate to replicate PD. Injections of the 6-OHDA solution were made into the left medial forebrain bundle (stereotaxic coordinates AP −5.0, L 1.3, V 8.0 form the dura mater) while under ketamine cocktail anesthesia (50 mg/kg, IP).

One experimental group received a subcutaneous transplantation of NO-releasing polymeric pellets, as described above, at the time of surgery. The second group received a subcutaneous transplantation of the same pellets in dialysis bag, as described above, at the time of surgery. The control group received pellets not containing the NO-releasing polymer.

Every three days post-surgery, each animal's Parkinsonian symptoms were assessed using the behavioral tests which consisted of the open field monitor, drag, and paw placement tests, as described above.

At 21 days post-surgery, animals received an injection of a dopamine agonist, apomorphine (0.1 mg/kg body weight) or levodopa (20.0 mg/kg body weight), to assess the degree of Parkinsonian symptoms, i.e., to assess contralateral rotational behavior, an index of Parkinsonian severity.

As shown in FIG. 2, subcutaneous transplantation of NO-polymer pellets significantly reduced the contralateral turning, an index of Parkinsonism. Three weeks after 6-OHDA surgery, total number of rotations were significantly reduced in animals transplanted with NO-releasing polymer pellets, *p<0.05. Because the experimental group was less affected by the 6-OHDA lesions, the results demonstrated that NO releasing polymers may have had a neuroprotective effect.

As shown in FIG. 3, subcutaneous transplantation of NO-releasing polymers (utilizing dialysis bags delivery) also significantly reduced the contralateral turning. Three weeks after 6-OHDA surgeries, total number of rotations was significantly reduced in animals transplanted with NO-polymer dialysis bag delivering different amounts of NO (0.05-0.5 mM blood plasma concentration of NO). Animals transplanted with NO-polymer dialysis bag delivering control pellets did not show any anti-Parkinsonian effect. The results also demonstrate that NO dysfunction may be an important participant in the pathogenesis of Parkinson's motor symptoms.

Figure 4:
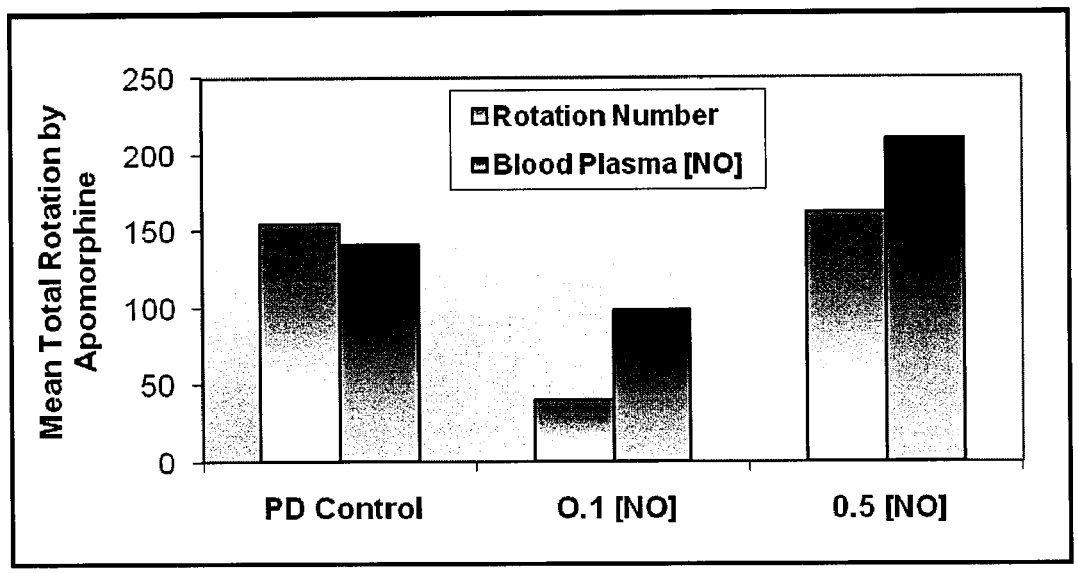
FIG. 4 is a graph representing Parkinsonian-induced symptoms and NO plasma level as a formation of NO continuation in Sprague-Dawley rats.

As shown in FIG. 4, in the experimental group, the blood plasma levels of NO were increased using the dialysis bag delivery method.

Other studies were performed that included testing initial efficacy of the NO releasing polymers and observing that animals that received the NO release polymer evidenced significant delay in their paw placement deficits. The results suggest that the NO therapy with the NO-releasing polymers can delay the onset of the severity of paw placement deficits characteristic of the akinesia-like motor responses observed in Parkinsonian patients.

Example 3

Soluble NO study

Male Sprague-Dawley rats weighing 200-250 g were housed with free access to food and water. Under sodium pentobarbital anesthesia (50 mg/kg, i.p.), the nigrostriatal pathway was unilaterally lesioned by administering 6-OHDA HCl (8 µg in 4 µL of saline with 0.02% ascorbate) into the left medial forebrain bundle (AP −5.0, L 1.3, V 8.0 from the dura matter). NO transfer into the substantia nigra was achieved by the local intracerebral administration of soluble NO donor of formula (VII) at 0.8, 0.08, or 0.008 µg in triethylene glycol dissolved in phosphate buffered saline at pH 7.4, or an equal volume of vehicles. Rats were anesthetized with pentobarbital (50 mg/kg, i.p.) and placed in a stereotaxic apparatus. NO donor stocks in 4.0 µL of solution or phosphate buffered saline vehicle were delivered by a syringe pump (Hamilton) into the left substantia nigra compacta (ipsilateral to the 6-OHDA lesion) at a rate of 0.5 µL/min for 4 min. After injection, the syringe was kept in place for an additional 3 to 4 min to allow diffusion of the drug solution. Rats received the NO donor stock or vehicle on the same day as the 6-OHDA lesioning and subsequently tested for Parkinsonian symptoms by performing apomorphine-induced contralateral rotation 21 days after surgery. On each apomorphine testing, animals were tested for their rotational response to an acute apomorphine challenge subcutaneously (0.05 mg/kg of apomorphine dissolved in sterile saline).

After three weeks of 6-OHDA lesioning plus soluble NO donor transfer into the substantia nigra, the total number of contralateral rotation response to apomorphine decreased by 95% and 68% in animals that received low and medium (0.008 and 0.08 µg) dose of NO donor, respectively (p<0.05; FIG. 5). Parkinsonian rats microinjected with low to medium doses of NO showed significant anti-Parkinsonian effect (i.e. lack of contralateral rotation) in response for the initial 3 weeks following NO treatment (FIG. 5). In a control experiment, NO transfer at all doses tested failed to alter the motor response to apomorphine in rats given sham lesion instead of 6-OHDA lesion.

PROPHETIC EXAMPLES

Example 4

Subcutaneous Implantation of NO-Releasing Polymer in Human Subjects Presenting Parkinson's Disease Symptoms Patients diagnosed with Parkinson's Disease (PD) within the past two years participate in a double blind, placebocontrolled study of subcutaneously-implanted NO-releasing polymers according to the present invention. The goal of the study is to determine if implantation of NO-releasing polymers slows the clinical decline in PD patients defined by a number of cognitive, physical, and quality of life measures.

All patients in the test will receive a subcutaneous implant of a polymer rod. The control group receives non-NO-releasing polymers of the type shown in formula (VI), while the test group receives NO-releasing polymers of the type shown in formula (III). Patients receive a monthly dosage of about 35 mg/kg, however dosage amount and interval may be adjusted during the course of the study to provide plasma levels of the active moiety which are sufficient to maintain the desired effects, termed the minimal effective concentration (MEC).

Patients participating in the study are screened at two week intervals for progression of PD using known tests such as Schwab & England, PDQ-39, Modified Rankin, etc. Patients receiving subcutaneous implants of polymers shown in formula (III) present a slower progression of PD, in comparison to the control group, as judged by the above tests.

In summary, the administration of NO-releasing polymers may confer novel and effective pharmacological therapeutic strategies for treatment of Parkinson's disease, especially in relation to NO pathways as potential pharmacological targets. The findings herein further demonstrate that controlled and sustained release formulation of NO-releasing polymers used in the protocol may also be useful for testing efficacy of exogenous NO donors potentially beneficial in the treatment and management of other serious medical conditions than Parkinson's Disease, including cardiovascular, oncogenic and neurodegenerative diseases.

All patents, publications, references and data cited herein are hereby fully incorporated by reference. In case of conflict between the present disclosure and incorporated patents, publications, references and data, the present disclosure should control.

We claim:

1. A medical device comprising an NO-releasing polymer of formula (I):

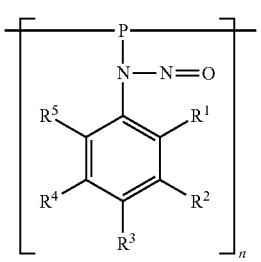

wherein P is a polymeric species with a chemical moiety capable of forming a covalent bond with N, and n is an integer greater than about 20, and $R^1$, $R^2$, $R^3$, $R^4$, and $R^5$ are H, F, or $NO_2$ provided that when $R^1$=F, then $R^2$, $R^3$, $R^4$, and $R^5$=F; and provided that when $R^1$=$NO_2$, then $R^2$, $R^3$, $R^4$, and $R^5$=H; provided that when $R^5$=$NO_2$, then $R^1$, $R^2$, $R^3$, and $R^4$=H; when $R^2$=$NO_2$, then $R^4$=$NO_2$ and $R^1$, $R^3$, and $R^5$=H; and when $R^3$=$NO_2$, then $R^1$, $R^2$, $R^4$, and $R^5$=H;

formula (II):

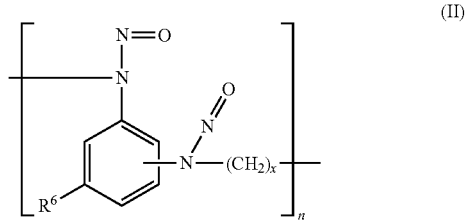

wherein x=2 to 12 and n is an integer greater than about 20, and $R^6$ is $NO_2$, CN, $CF_3$, or phenyl sulfone;

formula (III):

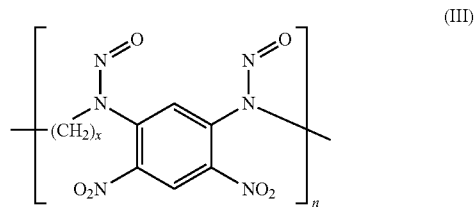

wherein x is 2 to 20 and n is an integer greater than about 20; or a combination thereof.

2. The medical device of claim 1, wherein the medical device is device selected from the group consisting of stents, vascular grafts, pacemaker leads, heart valves, electrodes, sensors, trocars, guide wires, catheters, penile implants, condoms, ocular lenses, sling materials, sutures, wound dressings/bandages, blood collection bags and storage tubes, and tubing used for blood transfusions and hemodialysis.

3. The medical device of claim 1, wherein the medical device is designed to be implanted into a bodily site.

4. The medical device of claim 3, wherein the bodily site is chosen from the group consisting of organs, tissues, membranes, cavities, blood vessels, tracts, biological surfaces, and muscles.

5. A medical device comprising a polymer of formula (IV):

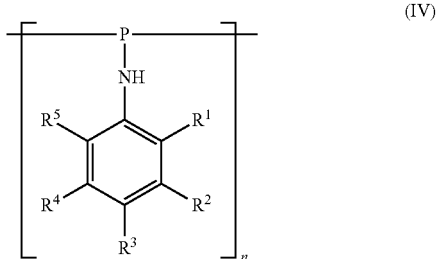

wherein P, n, $R^1$, $R^2$, $R^3$, $R^4$, and $R^5$ have the same meaning as described above for formula (I);

formula (V):

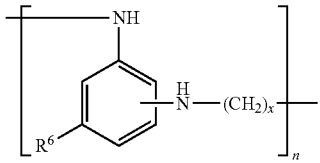

(V)

wherein x, n and $R^6$ have the same value as described in formula (II);

formula (VI):

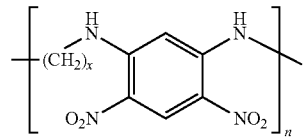

(VI)

wherein x=2 to 12 and n is an integer greater than about 20; or a combination thereof.

6. The medical device of claim 5, wherein the medical device is device selected from the group consisting of stents, vascular grafts, pacemaker leads, heart valves, electrodes, sensors, trocars, guide wires, catheters, penile implants, condoms, ocular lenses, sling materials, sutures, wound dressings/bandages, blood collection bags and storage tubes, and tubing used for blood transfusions and hemodialysis.

7. The medical device of claim 5, wherein the medical device is implanted into a bodily site.

8. The medical device of claim 7, wherein the bodily site is chosen from the group consisting of organs, tissues, membranes, cavities, blood vessels, tracts, biological surfaces, and muscles.

* * * * *